United States Patent [19]

Kita et al.

[11] 4,098,653
[45] Jul. 4, 1978

[54] OXYGEN SENSOR HAVING PROTECTIVE HOOD AND METHOD OF USING SAME

[75] Inventors: Toru Kita; Takeshi Fujishiro, both of Yokohama, Japan

[73] Assignee: Nissan Motor Company, Limited, Yokohama, Japan

[21] Appl. No.: 771,780

[22] Filed: Feb. 24, 1977

[30] Foreign Application Priority Data

Feb. 24, 1975 [JP] Japan .................................. 51-18524

[51] Int. Cl.² ........................................... G01N 27/46
[52] U.S. Cl. ................................. 204/1 T; 204/195 S
[58] Field of Search ............................. 204/15, 195 S

[56] References Cited

U.S. PATENT DOCUMENTS

| 3,546,086 | 12/1970 | Sayles | 204/195 S |
|---|---|---|---|
| 3,835,012 | 9/1974 | Hemak | 204/195 S |
| 3,844,920 | 10/1974 | Burgett et al. | 204/195 S |
| 3,960,692 | 6/1976 | Weyl et al. | 204/195 S |
| 3,960,693 | 6/1976 | Weyl et al. | 204/195 S |

FOREIGN PATENT DOCUMENTS

| 2,348,505 | 4/1975 | Fed. Rep. of Germany ... | 204/195 S |
|---|---|---|---|
| 2,351,815 | 4/1975 | Fed. Rep. of Germany. | |
| 2,416,629 | 10/1975 | Fed. Rep. of Germany. | |

Primary Examiner—T. Tung
Attorney, Agent, or Firm—Bacon & Thomas

[57] ABSTRACT

An oxygen sensor particularly useful for detecting oxygen concentration in exhaust gas of internal combustion engine is principally made up of a solid electrolyte tube which is closed at one end, anode and cathode electrode layers respectively formed on the outer and inner surfaces of the electrolyte tube and a tubular metal shell which tightly receives therein the electrolyte tube, leaving a closed end portion of the electrolyte tube protruded from the shell. To protect the protruded portion of the electrolyte tube against a direct exposure to a high velocity hot gas stream to be measured and a collision with any external article, without obstructing a rapid and uniform heating of the electrolyte tube by the gas stream, a hood in the shape of a cylindrical tube with a closed end is fixed at its open end portion to the shell to enclose therein the closed end portion of the electrolyte tube. The hood has a single gas inlet aperture formed in the side wall to extend axially of the hood and open against the gas stream and at least one gas outlet aperture formed in the side wall circumferentially at approximately 180° from the inlet aperture. The total area of the outlet aperture is smaller than the area of the inlet aperture.

17 Claims, 14 Drawing Figures

OXYGEN SENSOR HAVING PROTECTIVE HOOD AND METHOD OF USING SAME

This invention relates to an oxygen sensor for detecting oxygen concentration in a gas stream such as an exhaust gas stream in an automotive engine exhaust line, which sensor has an oxygen ion conductive solid electrolyte in the form of a tube closed at one end and a protective hood which takes the form of a perforated cup and encloses therein a closed end portion of the electrolyte tube to be disposed in the gas stream.

An oxygen sensor which includes a layer of an oxygen ion conductive solid electrolyte such as stabilized zirconia and operates on the principle of an oxygen concentration cell is well known. This type of oxygen sensor is suitable for detecting oxygen concentration in exhaust gas of an automotive engine as an element of a feedback control system for controlling the air-to-fuel ratio of an air-fuel mixture fed to the engine.

In practical application of this oxygen sensor to an automotive exhaust line, the solid electrolyte layer is usually formed into the shape of a tube which is closed at one end for convenience of attachment to either an exhaust manifold or an exhaust pipe and exposure of the electrolyte layer at its one side to the exhaust gas and at the opposite side to the atmospheric air as a reference gas. The outer and inner surfaces of the electrolyte tube are coated with porous (permeable to gas) and electron conductive layers, which are usually of platinum, respectively as the anode and cathode electrodes of the oxygen concentration cell.

To facilitate a clear understanding of the objects of the invention, a typical conventional oxygen sensor for automotive use will be described with reference to part of the accompanying drawings, wherein.

Figure 1:
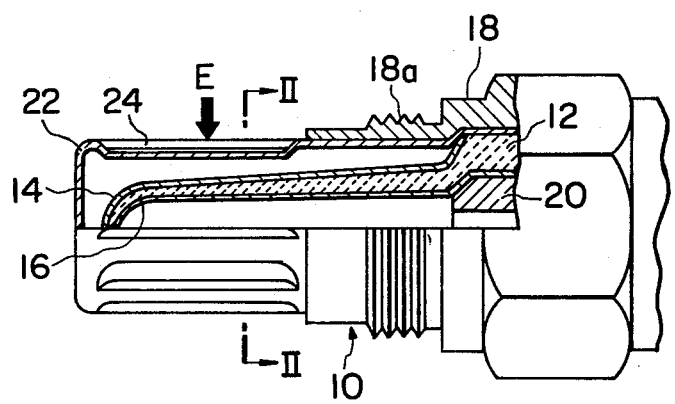
FIG. 1 is an elevational view, partly in section, of an essential portion of a conventional oxygen sensor.
Figure 2:
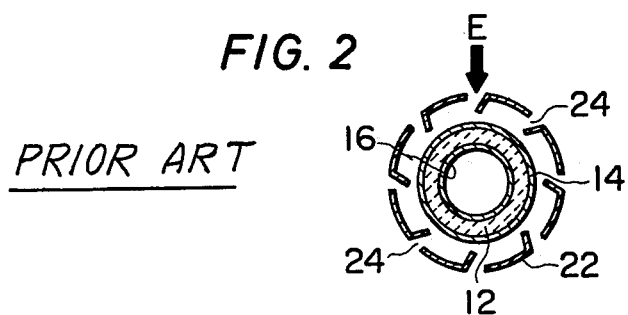
FIG. 2 is a cross-sectional view taken along the line II—II of FIG. 1.
Figure 3:
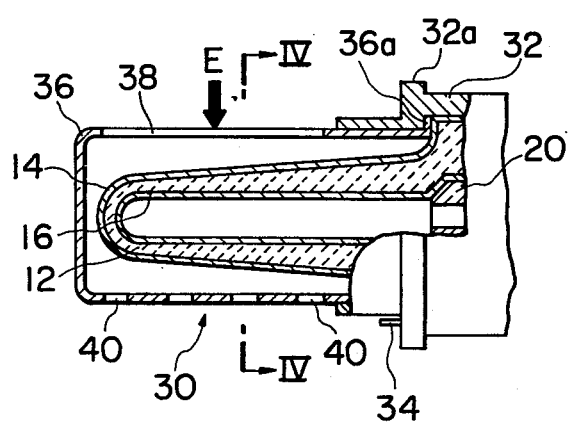
FIG. 3 is an elevational view, partly in section, of an essential portion of an oxygen sensor according to the invention.
Figure 6B:
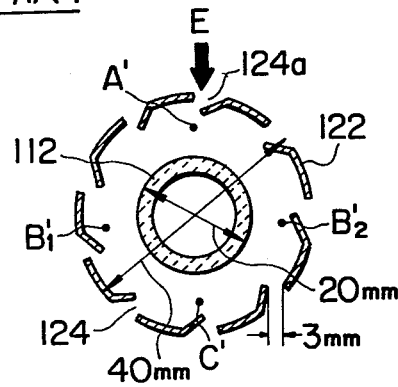
Figure 6A:
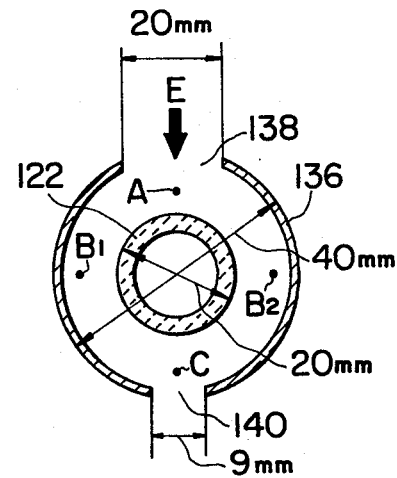
Figure 7:
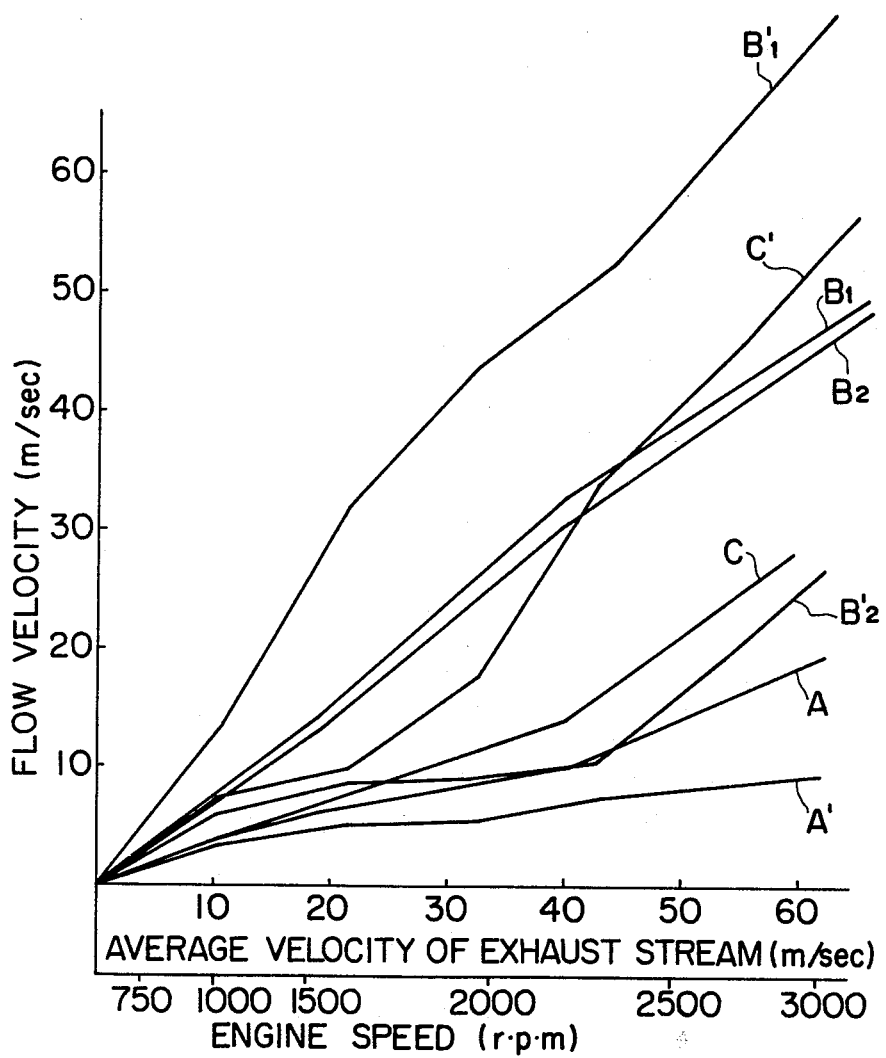
Figure 8:
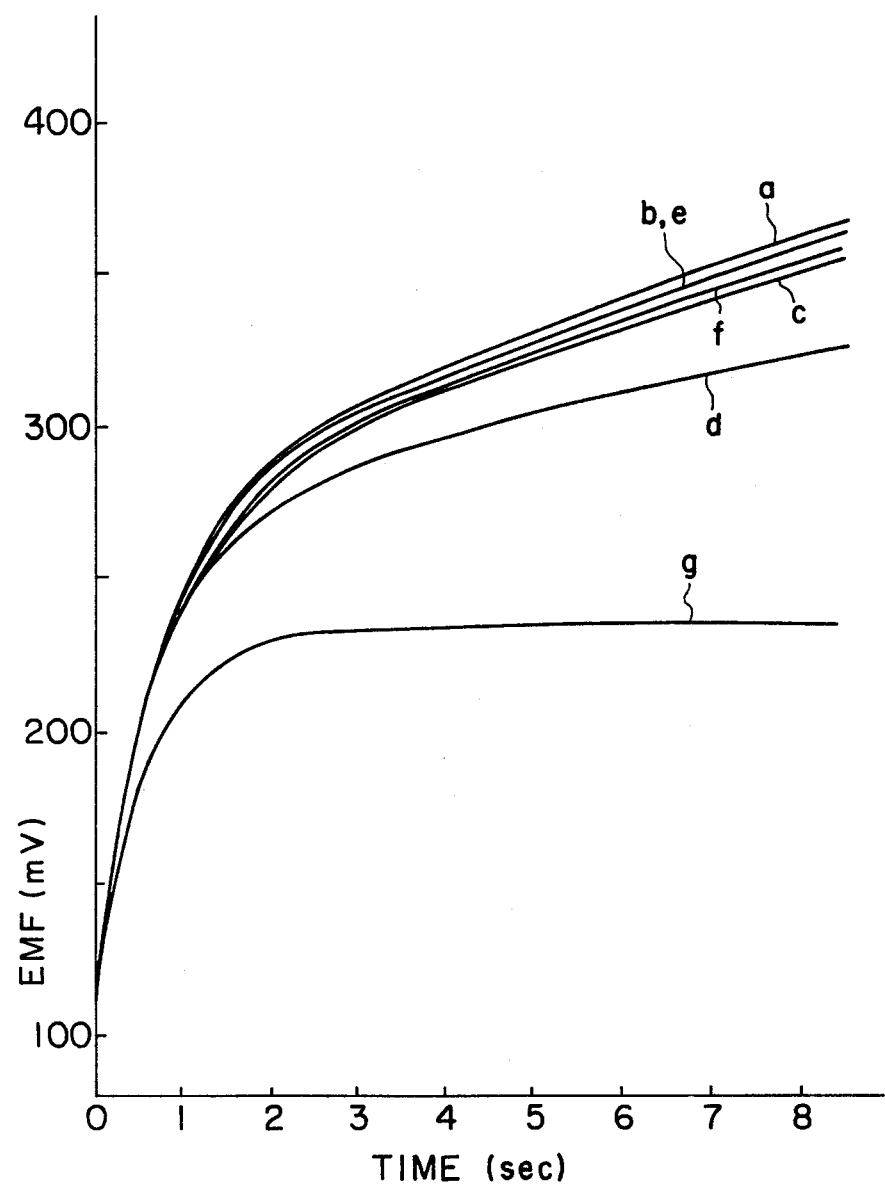

FIG. 5-a to FIG. 5-f are partly sectional elevations of six differently perforated protective hoods, respectively for the sensor of FIG. 2;

FIG. 6-a is a cross-sectional view showing a protective hood which is of the type illustrated in FIG. 5-a and used as a specimen in a comparative experiment carried out for confirming the effect of the invention;

FIG. 6-b is a cross-sectional view showing a protective hood of a conventional type used as another specimen in the same experiment;

FIG. 7 is a graph showing variations in the velocity of exhaust gas flow measured within the protective hoods of FIGS. 6-a and 6-b in the aforementioned experiment with variations in average velocity of an exhaust gas stream in which the hoods are disposed; and FIG. 8 is a graph showing variations in low temperature output characteristic of the oxygen sensors of FIG. 1 and FIG. 3 disposed in an exhaust gas stream.

Referring to FIG. 1, which shows a conventional oxygen sensor 10 for use in an exhaust line of an automotive engine, a solid electrolyte tube with a closed end is indicated at 12. An anode electrode layer 14 and a cathode electrode layer 16 are coated respectively on the outer and inner surfaces of the electrolyte tube 12. The electrolyte tube 12 coated with the electrode layers 14, 16 is tightly inserted into a tubular metal shell 18 such that a closed end portion of the tube 12 protrudes from the shell 18. This shell 18 has on its outside an attachment means such as screw threads 18a for attachement of the sensor 10 to the exhaust line so that the protruded portion of the electrolyte tube 12 may be disposed in an exhaust gas stream. The shell 18 serves also as an anode conductor. A metal tube 20 is inserted into the electrolyte tube from the open end to serve both as a cathode conductor and as an air-admitting conduit. When the anode side of the electrolyte tube 12 is exposed to a hot exhaust gas and the cathode side to air, an electromotive force is generated across the anode and cathode conductors 18 and 20. The magnitude of this electromotive force varies according to the oxygen concentration in the exhaust gas relative to the oxygen concentration in air admitted into the interior of the tube 12. In the exhaust line, the electrolyte tube 12 is usually oriented to lie generally normal to the direction of the exhaust gas stream (indicated by the arrow E).

As an element of practical importance, the sensor 10 has a shield or protective hood 22 which is made of a refractory material such as a metal and has the shape of a cup or a cylindrical tube with a closed end. This hood 22 is fixed at its open end region to the shell 18 so as to enclose therein the protruded portion of the electrolyte tube 12. The inside of the hood 22 is spaced from the anode electrode layer 14. As seen in FIGS. 1 and 2, a plurality of axial slits 24 are formed in the side wall of the hood 22 with circumferential intervals so that the exhaust gas may pass through the interior of the hood 22 and contacts the anode electrode layer 14.

The sensor 10 is provided with this hood 22 for preventing the electrolyte tube 12 from cracking or breaking by heat shocks resulting from direct exposure to a high temperature exhaust gas stream and protecting the tube 12 against collision with any article during handling of the sensor 10.

However, this type of hood 22 has some shortcomings. Firstly, the hood 22 has a significant shielding effect on the electrolyte tube 12 against the exhaust gas, so that the tube 12 cannot readily be heated to a suitable temperature when the exhaust gas temperature is not sufficiently high as experienced immediately after starting of the engine or at low engine speeds. Secondary, the exhaust gas does not uniformly flow within the hood 22 along the outside of the electrolyte tube 12: there is a considerable dispersion of flow velocity if the velocity is measured at various locations in the interior of the hood 22. As a result, a nonuniform temperature distribution occurs in the anode layer 14 and sometimes causes breakage of the anode layer 14. Besides, the provision of the multiple slits 24 to the hood 22 needs complicated procedures and accordingly leads to high production costs.

It is an object of the present invention to remedy these shortcomings of the conventional protective hood in an oxygen sensor of the described type.

It is another object of the invention to provide an improved oxygen sensor having an improved hood for the protection of a solid electrolyte tube of the sensor, which hood allows a gas stream to pass therethrough at moderately and almost uniformly reduced velocities without offering unduly great obstruction to the contact of the gas stream with the electrolyte tube.

An oxygen sensor according to the invention has an oxygen ion conductive solid electrolyte tube which is closed at one end, anode and cathode electrode layers porously formed respectively on the outer and inner surfaces of the electrolyte tube and a tubular metal shell tightly receiving therein the electrolyte tube such that a closed end portion of the tube protrudes from the shell and is disposable in a gas stream to be measured. As the feature of the invention, the sensor includes a protective hood which has the shape of a cylindrical tube with a closed end and is fixed at its open end portion to the shell so as to enclose therein the closed end portion of the electrolyte tube protruding from the shell. The inside of this hood is spaced from the anode electrode layer. The hood has a single gas inlet aperture formed in its side wall in an elongate shape to extend axially of the hood and at least one gas outlet aperture formed in the side wall to be located at an angle of approximately 180° with the gas inlet aperture in cross-sectional view of the hood. In this hood, the total area of the gas outlet aperture is smaller than the area of the gas inlet aperture. Because of the employment of this hood, the shell is provided with a locating means for attaching the sensor to an article, in which a gas to be measured streams, in a definite orientation such that the gas inlet aperture opens against the stream of the gas.

The gas outlet aperture of the hood may consist of a plurality of holes which are arranged substantially in a file parallel to the longitudinal axis of the hood with intervals, preferably with equal intervals, between each other. Alternatively, the gas outlet aperture may take the form of either a single elongate slot or a plurality of slots extending substantially parallel to the gas inlet aperture.

Other features and advantages of the invention will fully be understood from the following detailed description of preferred embodiments with reference to the drawings.

Figure 4:
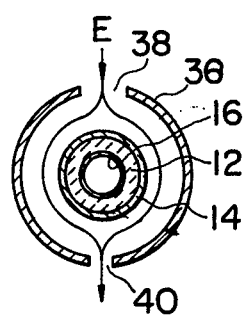
FIG. 4 is a cross-sectional view taken along the line IV—IV of FIG. 3.
Figure 5A:
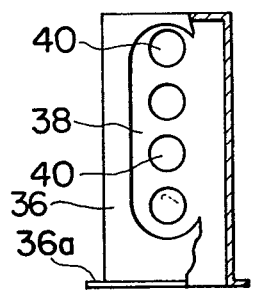
Figure 5B:
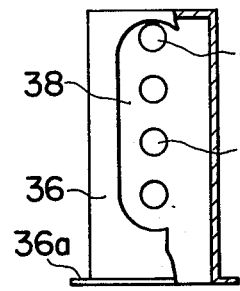
Figure 5C:
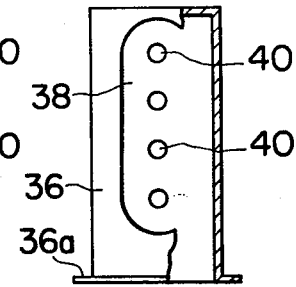
Figure 5D:
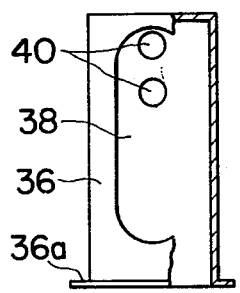
Figure 5E:
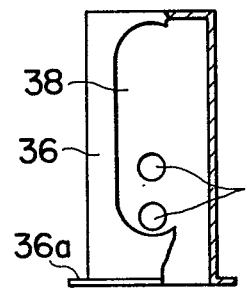
Figure 5F:
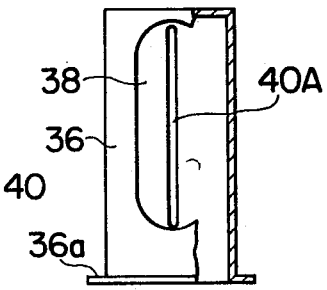

Referring to FIGS. 3 and 4, an oxygen sensor 30 according to the invention is principally of the same type as the conventional oxygen sensor 10 of FIG. 1. The solid electrolyte tube 12, anode and cathode electrode layers 14 and 16, and the tubular cathode conductor 20 are respectively identical with ones in the conventional sensor 10. An open end portion of the electrolyte tube 12 of this sensor 30 is tightly inserted into a tubular metal shell 32 which serves also as an anode conductor. Instead of threading the outside of this shell 32, a flange 32a is formed on the wall of the shell 32 in a region close to an end from which the closed end portion of the electrolyte tube 12 protrudes. A locating pin 34 stands on one end face of this flange 32a facing the closed end of the electrolyte tube 12. The shell 32 has the flange 32a and locating pin 34 for enabling to attach the sensor 30 to a boss, which is formed on an exhaust pipe and has either a hole or a slot in a definite position, by pressing the flange 32a against an end face of the boss by means of a cap nut (not shown). As will be understood from the subsequent description, it is intended to dispose the sensor 30 in an exhaust gas stream to lie substantially normal to the gas stream and circumferentially in a definite arrangement relative to the direction of the stream.

A protective hood 36 having the shape of a cup or cylindrical tube with a closed end is fixed at its open end portion to the shell 32 so as to enclose therein the protruded portion of the electrolyte tube 12. It is convenient to fix the hood 35 to the inside of the shell 32 by forming a flange 36a at the open end of the hood 36 and a shoulder on the inside of the shell 32. The dimensions of the hood 36 are such that the inside of the hood 36 is entirely spaced from the electrolyte tube 12 at the outside of the shell 32.

To admit the exhaust gas into the interior of the hood 36, an elongate (axially of the hood 36) or generally rectangular aperture 38 is formed in the side wall of the hood 36. This aperture 38 extends approximately from the end of the shell 32 to a plane tangent to the outside of the closed end of the electrolyte tube 12. The aperture 38 is in a definite angular relation with the locating pin 34 such that the aperture 38 opens against the exhaust stream E or normal to the direction of the stream in plan view of the sensor 30 as shown in FIG. 4 when the sensor 30 is attached to the exhaust pipe. A plurality of (four in the illustrated case) holes 40, which are all identical, are formed in the side wall of the hood 36 arranged in a file parallel to the axis of the tubular hood 36 with nearly equal intervals therebetween. As seen in FIG. 4, the file of these holes 40 is substantially at an angle of 180° with the elongate aperture 38, that is, the holes 40 are distant from the aperture 38 by substantially the diameter of the hood 36. Accordingly, a plane which cuts both the aperture 38 and the holes 40 are nearly parallel to the exhaust gas stream E. The exhaust gas enters the interior of the hood 36 through the aperture 38 and leaves the hood 36 through the holes 40. The hood 36 has no extra hole or slit in other regions. As a matter of importance, the total area of the holes 40 is smaller than the area of the elongate aperture 38.

When the sensor 30 is disposed in the exhaust gas stream E to take the above described angular position, the exhaust gas can freely enter the interior of the hood 36 since the aperture 38 is not so narrow as to be called slit but has a substantial width. Accordingly the electrolyte tube 12 is sufficiently exposed to the exhaust gas and can readily be heated. However, the exhaust gas flows in the hood 36 at velocities lower than its average velocity at the outside of the hood 36 because the smallness of the total area of the outlet holes 40 offers a resistance to the flow of the exhaust gas in the hood 36. The anode electrode layer 14, therefore, can be protected against being locally damaged by the collision of the exhaust gas at excessively high velocities. Furthermore, the exhaust gas flows in the hood 36 almost uniformly along the outer circumference of the electrolyte tube 12, so that the tube 12 can uniformly be heated. Consequently, the employment of the hood 36 gives rise to an improved low temperature output characteristic and a prolonged service life of the sensor 30.

As will readily be understood, the small holes 40 can be formed variously in their individual shape and size and/or total number. Some examples are presented in FIG. 5-a to FIG. 5-f. In these examples, the hood 36 has the shape of a cylindrical tube, about 13 mm in outer diameter and about 25 mm in length, with a closed end and a flange 36a at the open end. The gas inlet aperture 38 has an elongate shape parallel to the axis of the hood 36 and is about 7 mm wide and about 20 mm long throughout these examples.

In FIG. 5-a, the gas outlet holes 40 are four in total and arranged in a file parallel to the longitudinal axis of the aperture 38 to entirely be contained, in an elevational view of the hood 36, in the area of the aperture 38. Each of these holes 40 is circular with a diameter of about 4 mm (so that the ratio P of the total area of the holes 40 to the area of the aperture 38 is about 1:3).

In FIGS. 5-b and 5-c, the outlet holes 40 are formed in the same manner as in FIG. 5-a except that they have smaller diameters. In FIG. 5-b each of the holes 40 is about 3 mm in diameter, so that the above defined area ratio P is about 1:5. In FIG. 5-c, the diameter is about 2 mm and the ratio P about 1:12.

In the case of FIG. 5-d, the outlet holes 40 are only two in total and located relatively close to the closed end of the hood 36 (to be contained in a half area of the elongate aperture 38 in the elevational view). These two holes 40 are individually circular with a diameter of about 3 mm, so that the ratio P is about 1:10. In FIG. 5-e, the holes 40 are formed generally in the same manner as in FIG. 5-d except that the two 3 mm diameter holes 40 are located relatively close to the open end of the hood 36.

In FIG 5-f, the hood 36 has only one slot 40A as a gas outlet in place of the multiple circular holes 40 in the preceding examples. This slot 40A is about 1.5 mm wide and about 20 mm long and extends parallel to the elongate inlet aperture 38 to entirely be contained in the area of the aperture 38 in the elevational view. The ratio P is about 1:5 in this case. It is permissible to replace this slot 40A by a plurality of shorter slots.

Regardless of the shape and total number of the holes 40 (or the slot 40A), it is preferable to determine the area ratio P within the range from about 1:2 to about 1:5.

An experiment was carried out to examine the effect of the hood 36 according to the invention in comparison with the conventional hood 22 as shown in FIGS. 1-2. To measure the flow velocity of the exhaust gas at various locations in the respective hoods, the experiment was carried out on model specimens which were about three times as large as the practical hood 36 (or 22) enclosing therein a similarly enlarged model 112 of the electrolyte tube 12.

FIG. 6-a shows a model 136 of the hood 36 enclosing therein the electrolyte tube model 112 of 20 mm diameter. The model hood 136 was 40 mm in outer diameter and about 75 mm in length. The elongate aperture 138 and the circular holes 140 of this model hood 136 were designed as shown in FIG. 5-b. The aperture 138 was 20 mm wide and about 60 mm long, and each of the four holes 140 was 9 mm in diameter (the ratio P was about 5). FIG. 6-b shows the model 122 of the conventional hood 22. This model hood 122 also was 40 mm in outer diameter and about 75 mm in length, and nine slits 124, each 3 mm wide and about 60 mm long, were formed with circumferentially equal intervals therebetween.

These models 136 and 122 were disposed in an exhaust gas stream E as seen in FIGS. 6-a and 6-b, to measure the flow velocity of the exhaust gas within the respective models 136 and 122 at locations A, $B_1$, $B_2$ and C for the model 136 and at A', $B_1'$, $B_2'$ and C' for the model 122. Average velocity of the exhaust gas stream E at the outside of the model 136, 122 was varied by operating an engine at various r.p.m.

FIG. 7 shows the result of this experiment. In the model hood 122 of the conventional type, the exhaust gas came into collision with the electrolyte tube model 113 at a velocity apparently below an average velocity at the outside of the hood 122 as seen from the curve (A') for the location A', but a great difference in flow velocity was found between the two location $B_1'$ and $B_2'$ which were respectively on the right and left sides of a plane containing the axis of the model tube 112 and the axis of a principal inlet slit 124a. Naturally, the model tube 112 might be heated at a relatively low efficiency and significantly nonuniformly. In the model hood 136 of the novel type, the flow velocity at the location A was satisfactorily low compared with average velocity at the outside despite the enlarged width of the inlet aperture 138. There was substantially no difference in flow velocity between the two locations $B_1$ and $B_2$ (respectively on the right and left sides of the aperture 138) in this model hood 136. Accordingly the model tube 112 might be heated almost uniformly at an improved efficiency in this case. The flow velocity at the location $B_1$ or $B_2$ was higher than the velocity at A but yet lower than average velocity at the outside. If it is desired to further lower the velocity at $B_1$ and $B_2$, the desire can be met by decreasing the total area of the outlet holes 140 to make the area ratio P more close to 1:15 (P was about 1:5 in this experiment).

Another experiment was carried out to examine the effect of the hood 36 according to the invention on the low temperature output characteristic of the sensor 30 in comparison with the conventional hood 22. The sensor 10 of FIG. 1 and the sensor 30 of FIG. 3 were disposed in an exhaust pipe of an automotive engine which was operated at low r.p.m. so that the exhaust gas temperature was 320°–350° C. The air-to-fuel ratio of an air-fuel mixture fed to the engine was abruptly varied from an excess air state to a fuel-rich state during operation of the engine, and the electromotive force generated by the sensors 10 and 30 was continuously measured from the moment of the switch-over of the air-to-fuel ratio. The experimental result is presented in FIG. 8, wherein the curves (a) – (f) respectively, represent the six designs of the hood 36 according to FIGS. 5-a to 5-f employed in the sensor 30, and the curve (g) represents the conventional sensor 10 having the hood 22. As seen in FIG. 8, the oxygen sensor 30 according to the invention exhibits, when disposed in a considerably low temperature exhaust gas stream, a greatly improved responsiveness to a variation in the oxygen concentration in the exhaust gas compared with the conventional sensor 10, which operates on the same principal as the sensor 30 does. Furthermore, the improved sensor 30 generates an electromotive force of a greater magnitude than the conventional sensor 10 under the same condition. The improved responsiveness and augmented electromotive force of the improved sensor 30 imply that the electrolyte tube 12 in this sensor 30 is more readily and uniformly be heated by the exhaust gas than in the conventional sensor 10.

What is claimed is:

1. An oxygen sensor for detecting oxygen concentration in the exhaust gas of an internal combustion engine, said sensor having an oxygen ion conductive solid electrolyte tube which is closed at one end, and open at the other end, anode and cathode electrode layers porously coated respectively on the outer and inner surfaces of the electrolyte tube and a tubular metal shell which tightly receives the electrolyte tube therein such that a closed end portion of the electrolyte tube protrudes from the shell and is adapted to be disposed in an exhaust gas stream, a protective hood which has the shape of a cylindrical tube with a closed end and is fixed at its open end portion to the shell, the inside of said hood being spaced from the anode electrode layer outside of the shell, said hood having a plurality of apertures formed in its wall to allow the gas to be measured to pass through the interior of said hood, the improvement comprising:

said hood having a gas inlet of a single aperture formed in the side wall of said hood in an elongate shape to extend axially of the hood, and a gas outlet formed in the side wall of said hood comprising at least one aperture, said gas outlet being located at an angle of approximately 180° with said gas inlet aperture in cross-sectional view of said hood, said gas outlet having a total area of opening which is smaller than the area of opening of said gas inlet aperture, and said shell having means for permitting attachment of the sensor to an article in which a gas to be measured flows in a definite orientation such that said gas inlet aperture opens facing the stream of said gas.

2. An oxygen sensor as claimed in claim 1, wherein said gas outlet consists of a plurality of apertures which are arranged substantially in a file parallel to the longitudinal axis of said hood with intervals between each other.

3. An oxygen sensor as claimed in claim 2, wherein said plurality of apertures are entirely contained in the area of said gas inlet aperture in an elevational view of the hood.

4. An oxygen sensor as claimed in claim 3, wherein said plurality of apertures are individually circular.

5. An oxygen sensor as claimed in claim 1, wherein said gas outlet takes the form of an elongate slot extending parallel to said gas inlet aperture.

6. An oxygen sensor as claimed in claim 1, wherein said gas inlet aperture extends substantially over the entire length of the closed end portion of the electrolyte tube protruded from the shell.

7. An oxygen sensor as claimed in claim 1, wherein the ratio of the total area of said gas outlet to the area of said gas inlet aperture is in the range from about 1:2 to about 1:15.

8. An oxygen sensor as claimed in claim 1, wherein said means for attaching the sensor comprise a flange formed on the outside of the shell and a locating pin protruding from an end face of said flange axially substantially parallel to the electrolyte tube.

9. An oxygen sensor as defined by claim 1, wherein said gas outlet consists of a single elongate slot.

10. An oxygen sensor as defined by claim 9, wherein said single elongate slot is equal to said gas inlet aperture in length and axial position.

11. An oxygen sensor for detecting oxygen concentration, said sensor comprising:
an oxygen ion conductive solid electrolyte tube which is closed at one end;
anode and cathode electrode layers respectively located on the outer and inner surfaces of said electrolyte tube;
a tubular metal shell adapted to receive said electrolyte tube therein such that a closed end portion of the electrolyte tube protrudes from the shell;
a protective hood having the shape of a cylindrical tube with a closed end and which is fixed at its open end portion to said shell, the inside wall of said hood being spaced from the anode electrode layer outside of said shell;
said hood comprising an inlet and a gas outlet comprising at least one aperture formed in said sidewall, and no other apertures formed in said sidewall, to permit passage of the gas to be measured through the interior of said hood;
said inlet and outlet in said hood being arranged at about 180° to one another so as to provide for even and uniform flow of said gas through said hood; and
said shell further comprising means permitting the attachment of said shell such that once attached, the apertures of said sensor assume the same orientation relative to said article every time said sensor is attached to said article.

12. The oxygen sensor as defined by claim 11 wherein the total area of said inlet aperture exceeds the total area of said outlet.

13. The oxygen sensor as defined by claim 12 wherein the ratio of the total area of said gas outlet to the area of said gas inlet aperture is in the range from about 1:2 to about 1:15.

14. The oxygen sensor as defined by claim 11 wherein said means permitting attachment of said sensor comprises a flange formed on the outside of the shell and a locating pin protruding from an end face of said flange which is substantially parallel to the axis of said electrolyte tube.

15. An oxygen sensor for detecting oxygen concentration, said sensor comprising:
an oxygen ion conductive solid electrolyte tube which is closed at one end;
anode and cathode electrode layers respectively located on the outer and inner surfaces of said electrolyte tube;
a tubular metal shell adapted to receive said electrolyte tube therein such that a closed end portion of the electrolyte protrudes from the shell; and
a protective hood having the shape of a cylindrical tube with a closed end and which is fixed at an open end portion to said shell, the inside sidewall of said hood being spaced from the anode electrode layer outside of said shell; and
said hood comprising a gas inlet of a single aperture formed in the sidewall of said hood and a gas outlet comprising at least one aperture located in said sidewall, said inlet and outlet being spaced from one another by approximately 180°.

16. The sensor as defined by claim 15 wherein the area of said inlet aperture is greater than the total area of said outlet.

17. A method of detecting the oxygen content of a gas stream which comprises the steps of:
(a) providing an oxygen sensor having an oxygen ion conductive solid electrolyte tube which is closed at one end, anode and cathode layers porously coated respectively on the outer and inner surfaces of said electrolyte tube, and a tubular metal shell which receives the electrolyte tube therein such that a closed end portion of the electrolyte tube protrudes from said shell and is adapted to be disposed in an exhaust gas stream, a protective hood which has the shape of a cylindrical tube with a closed end and is fixed at an open end portion to the shell, the inside of said hood being spaced from the anode electrode layer outside of said shell, said hood comprising a single outlet aperture and an outlet comprising at least one aperture, said inlet aperture being spaced from said outlet apertures by approximately 180°; said inlet aperture having a larger area than the total area of said outlet apertures;
(b) arranging said sensor in said gas stream such that said inlet aperture is arranged normal to the direction of flow of said gas stream and such that said outlet apertures are downstream of said inlet aperture in the direction of flow of said gas stream; and
(c) measuring the oxygen content of said gas stream.

* * * * *